Figure 1:
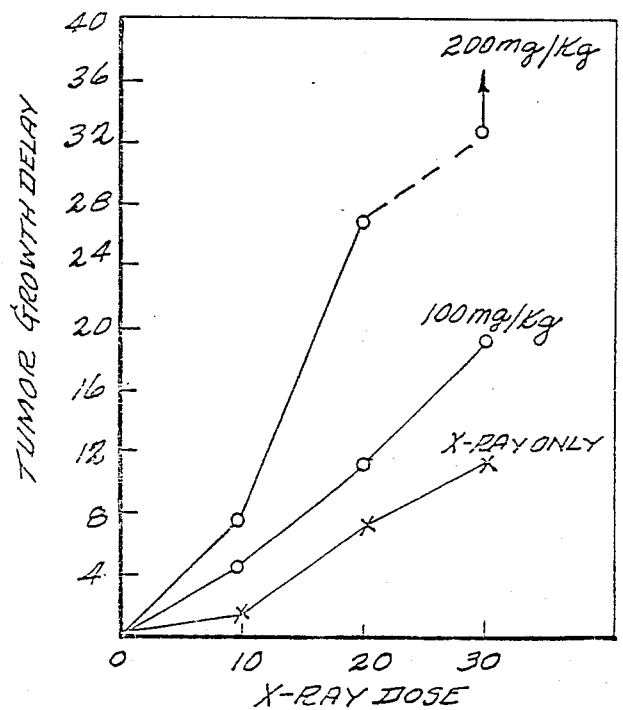

United States Patent [19]

Teicher et al.

[11] Patent Number: 4,921,973

[45] Date of Patent: May 1, 1990

[54] PLATINUM COMPLEXES AND THE LIKE

[75] Inventors: Beverly A. Teicher, Boston, Mass.; Robert C. Richmond, Hanover, N.H.; Lan B. Chen, Boston, Mass.

[73] Assignee: Johnson Matthey Inc., Forge, Pa.

[21] Appl. No.: 186,177

[22] Filed: Apr. 26, 1988

Related U.S. Application Data

[62] Division of Ser. No. 680,044, Dec. 10, 1984, abandoned.

[51] Int. Cl.$^5$ .............................................. C07D 311/88
[52] U.S. Cl. ...................................... 549/212; 549/227
[58] Field of Search ................ 549/212, 227; 514/184, 514/185

[56] References Cited

U.S. PATENT DOCUMENTS

| | | | |
|---|---|---|---|
| 4,457,926 | 7/1984 | Amundsen et al. | 514/184 |
| 4,462,998 | 7/1984 | Amundsen et al. | 514/184 |
| 4,490,543 | 12/1984 | Bergquist et al. | 549/212 |

FOREIGN PATENT DOCUMENTS

| | | |
|---|---|---|
| 167071A | 6/1984 | European Pat. Off. |
| 1037796 | 7/1984 | Japan . |

Primary Examiner—Richard L. Raymond
Assistant Examiner—Ba K. Trinh
Attorney, Agent, or Firm—Cushman, Darby & Cushman

[57] ABSTRACT

A (+)-charged dye transition metal complex, particularly a complex of platinum and a (+)-charged dye such as rhodamine 123. These products demonstrate antitumor and radio-sensitizing activity.

2 Claims, 1 Drawing Sheet

PLATINUM COMPLEXES AND THE LIKE

This is a division of application Ser. No. 680,044, filed Dec. 10, 1984, now abandoned.

BACKGROUND AND SUMMARY OF THE INVENTION

The present invention is concerned with a new group of metal complexes, particularly Pt complexes, which demonstrate antitumor activity. The complexes also possess radiosensitizing activity whereby cells or tissues can be made more sensitive to the killing effects of ionizing radiation when the complexes of the invention are used before, during, or after irradiation.

Broadly speaking, the complexes of the invention are (+)-charged dye complexes obtained by reacting a (+)-charged dye with a metal compound, preferably a platinum compound or compound of another platinum group metal, and more preferably a Pt(II) compound. A particularly preferred complex according to the invention is the product obtained by reacting a platinum(II) compound with rhodmaine-123, hereinafter referred to as Pt(Rh-123). However, generally similar complexes prepared by using other charged dyes, as described below, are also contemplated.

The complexes of the invention may be made by reacting an organic or inorganic platinum compound or the equivalent with rhodamine 123, which structurally may be illustrated as follows:

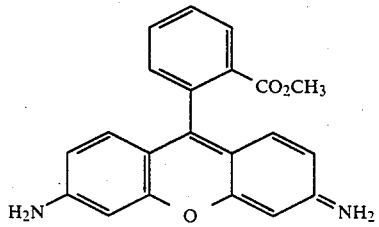

or other (+)-charged rhodamine or the like, for example, a cyanine dye such as:
- 3,3'-diethylthiadicarbocyanine iodide
- 3,3'-diethyloxatricarbocyanine iodide (027)
- 3,3'-diethyloxadicarbocyanine iodide
- 3,3'-diethylthiatricarbocyanine iodide stains all (SA),
  or other (+)-charged cyanine dyes,
- tetraarylphosphonium salts bearing amino, hydroxyl or mercapto substituents,
- decaqualinium chloride (Deca) or other (+)-charged organic compounds.

Typically suitable platinum compounds include potassium tetrachloroplatinate (II) or the like alkali metal tetrahaloplatinate (II); or cis-bis(acetonitrile)dichloroplatinum (II).

The reaction between the platinum compound and the rhodamine 123, or equivalents thereof, may be represented as follows, using potassium tetrachloroplatinate and rhodamine 123 for purposes of illustration:

$$K_2PtCl_4 + 2Rh\text{-}123 \rightarrow PtCl_2(Rh\text{-}123)_2 + 2KCl$$

The reaction is conveniently carried out by adding an organic or aqueous solution of the rhodamine 123 or equivalent to an organic or aqueous solution of the platinum compound, preferably while stirring, and allowing the reaction mixture to stand at room temperature (20°–25° C.) until the desired complex precipitates out. The precipitate may be separated and washed in conventional fashion to provide the product in an essentially pure state. Heat may be applied in some instances to facilitate the desired complexing reaction but usually it is adequate to employ temperatures in the order of 20°–25° C. The reaction is usually completed in 10–24 hours.

In some cases the molar ratio of dye to platinum compound is 2:1; in other cases equimolar amounts of the reactants may be used although this is not critical. In any case, not more than 25% molar excess of either reactant is usually employed.

The present complexes demonstrate antitumor activity as shown on standard tests using MB 49 bladder carcinoma, P388 and L1210 leukemias and Lewis lung carcinoma. Based on the degree of activity demonstrated in the experiment tumors, the present complexs should be useful for their antitumor activity in essentially the same way, including dosages and mode of administration, as known antitumor Pt-complexes, e.g. cisplatin.

The invention is illustrated, but not limited, by the following:

EXAMPLE 1

Potassium tetrachloroplatinate (II) (415 mg, 0.001 mmole) was dissolved with stirring in 20 ml of distilled, deionized water. To this solution was added slowly with stirring a solution of rhodamine-123 (76 mg, 0.0022 mole) in 15 ml of distilled, deionized water. The reaction vessel was covered to protect the reaction mixture from light. The reaction was allowed to stir at room temperature (20° C.) overnight, then was allowed to stand for 4 hours at 4° C. The dark red precipitate was collected by suction filtration and washed with 40 ml portions of ice cold 1N hydrochloric acid, ice cold distilled ionized water, ice cold methanol and ice cold diethyl ether. The yield ranged from 45–55%. The composition of the product (Pt(Rh-123)) was confirmed by elemental analysis as shown in Table 1.

EXAMPLE 2

Cis-bis(acetonitrile)dichloroplatinum (II) (392 mg, 0.001 mole) was dissolved with stirring in 20 ml of chloroform. To this solution was added slowly with stirring a solution of rhodamine-123 (762 mg, 0.0022 mole) in 15 ml of chloroform. The reaction vessel was covered to protect the reaction mixture from light. The reaction mixture was allowed to stir overnight at room temperature, then was concentrated to a volume of 10 ml. The concentrated solution was allowed to stand for 4 hours at 4° C., then the dark red precipitate was collected by suction filtration and washed with 40 ml portions of ice cold 1N hydrochloric acid, ice cold distilled dionized water, ice cold methanol and ice cold diethyl ether. The yield ranged from 80–90%. The composition of the product (Pt(Rh-123)) was confirmed by elemental analysis as set forth in Table 1.

TABLE 1

| | Elemental Analysis of Pt (Rh-123) | | | | | |
|---|---|---|---|---|---|---|
| | % C | % H | % N | % O | % Cl | % Pt |
| calculated for 5H$_2$O | 45.21 | 3.79 | 5.02 | 8.60 | 12.71 | 17.49 |
| found: | | | | | | |
| Example 1 | 45.13 | 3.96 | 5.01 | — | — | 17.45 |

TABLE 1-continued

| | Elemental Analysis of Pt (Rh-123) | | | | | |
|---|---|---|---|---|---|---|
| | % C | % H | % N | % O | % Cl | % Pt |
| Example 2 | 47.42 | 3.60 | 5.27 | — | — | 18.34 |

Other complexes according to the invention were prepared generally as described in Examples 1 or 2 except that 3,3'-diethyloxatricarbocyamine iodide (027), stains all (SA) and decaqualinium chloride (Deca) were used as the (+)-charged dye components in lieu of the rhodamine-123 to give products which may be identified for convenience as Pt 027, Pt SA and Pt Deca, respectively. The antitumor activity of Pt(Rh-123) and these other complexes was compared with that of a known platinum complex and the dye components themselves as shown hereinafter.

EXAMPLE 3

Antitumor activity for Pt(Rh-123) was assessed in four transplantable tumors: (1) MB49 bladder carcinoma, (2) P388 leukemia, (3) L1210 leukemia, and (4) Lewis lung carcinoma. In all cases, $10^6$ tumor cells were implanted intraperitoneally in mice on day 0 and drug treatment was begun on day 1.

The mice were thereafter treated with a non-toxic dose of Pt(Rh-123) or other (+)-dye Pt complex referred to above on an every other day schedule for days 1, 3, 5, 7, 9 and 11. The animals did not lose weight over the treatment period.

Pt(Rh-123) and the other (+)-dye Pt complexes on this schedule demonstrated significant activity in all of the test tumors as shown in Table 2. The antitumor activity of these complexes was comparable to or better than that for the known complex, cis-diamminedichloroplatinum (II) (CDDP). Activity data is also provided in Table 2 for the dye components themselves to show the significant improvement which results from complexing according to the invention.

TABLE 2

Survival of mice bearing various tumors treated with various Pt complexes.

| Drug | Dose, qd 2 × 6 (mg/kg) | Tumor % T/C | | | |
|---|---|---|---|---|---|
| | | P388 | L1210 | MB49 | Lewis Lung |
| CDDP | 4.5 | 125 | 175 | 147 | 200 |
| Pt (Rh-123) | 75 | 155 | 225 | 185 | 82 |
| Pt027 | 20 | 191 | 238 | 155 | 127 |
| PtSA | 3 | 155 | 225 | 179 | 136 |
| PtDeca | 10 | 127 | 250 | 197 | 179 |
| Rh-123 | 25 | 25 | 13 | 125 | 96 |
| 027 | 1.8 | 15 | 0 | 130 | 74 |
| SA | 1.0 | 22 | 25 | 155 | 110 |
| Deca | 4 | 36 | 38 | 1 | 54 |

P388 and L1210 are mouse leukemias. MB49 is a mouse bladder carcinoma and Lewis lung is a mouse lung carcinoma.

EXAMPLE 4

Radiosensitization Activity: In Vivo. The Lewis lung tumor was grown in B6D2Fl/J male mice (Jackson Laboratory) 8 to 10 weeks of age. There were seven animals in each group and the experiment was done twice. For the experiments, $2 \times 10^6$ tumor cells prepared from a brie of several stock tumors were implanted subcutaneously in the flanks of mice. When the tumors were approximately 50 mm$^3$ in volume (about 1 week after tumor cell implantation, the animals were treated with a single dose of Pt(Rh-123) of 100 mg/kg or 200 mg/kg administered by i.p. injection. The animals showed no toxicity from this dose of Pt(Rh-123).

One hour later the tumor-bearing limb was given a single dose of x-rays of 1000, 2000 or 3000 rads with a Gamma Cell 40 (Atomic Energy of Canada, dose rate; 88 rad per minute). The shielded portion of the animal received less than 2 percent of the delivered dose. Animals were anesthesized during the radiation treatment.

To determine the delay in tumor growth, the progress of each tumor was measured thrice weekly until it reached a volume of 500 mm$^3$. Untreated Lewis lung tumors reached 500 mm$^3$ in about 14 days. The tumor growth delay results are shown in FIG. 1. The dose modifying factor obtained with 100 mg/kg of Pt(Rh-123) was 1.6 and the dose modifying factor obtained with 200 mg/kg of Pt(Rh-123) was 2.1. To determine the dose modifying factor, zero growth delay was assumed with 0 rad and that factor which related the control dose of the same growth delay achieved with 1000 rads was calculated.

EXAMPLE 5

Radiosensitization Activity. In Vitro After Heating. A 200 4 μM solution of Pt(Rh-123) was heated to 90° C. in phosphate buffered normal saline. The resulting preparation was a superior radiosensitizer of hypoxic bacterial cells. Heating produced a preparation which was stable for many days (see FIG. 1).

Figure 2:
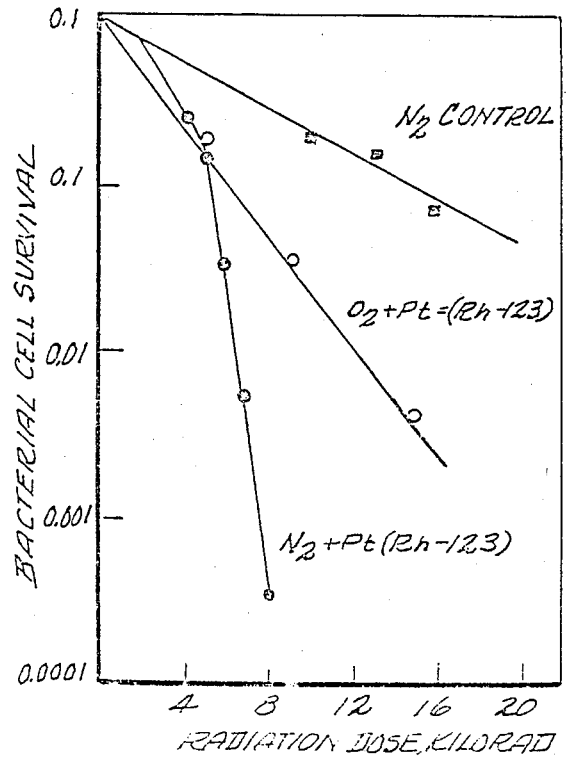

As shown in FIG. 2, the preheated drug preparation was not a radiosensitizer of oxygenated cells but produced an enhancement of greater that 3-fold in hypoxic cells.

While the invention has been exemplified above primarily on the basis of platinum complexes, particularly Pt(Rh-123), it will be appreciated that the invention is of broader application. Thus, the complexes of the invention may be structurally represented by the formula $R_2MX_2$ or, somewhat more broadly, $R_nMX_m$ where n and m are 1 or 2; R is Rh-123 or other mono- or divalent (+)-dye molecule; M is Pt(II) or other metal, e.g. another platinum group metal such as Rh, Ir, Pd, Au, Os, Ru, etc; and X is chlorine or other mono- or divalent leaving group.

Various modifications may be made in the invention as described above. Thus, for example, the cationic molecule used in the metal complex may be varied to enhance the desired effects of antitumor activity and radiation sensitization. The method of attachment of the dye to the metal may also be varied in order to enhance the desired effects. Thus, the dye may be attached to the metal center by ionic as well as coordinate binding. Additionally, as noted, the transition metal center may be varied from Pt in the dye complex in order to enhance the desired effects of antitumor activity and radiation sensitization. Thus, Au, Rh, Pd, Ir, Os, or Ru may be used in the synthesis of the invention.

Accordingly, the scope of the invention is defined in the following claims wherein:

We claim:

1. A complex obtained by reacting (1) alkali metal tetrahaloplatinate or cis-bis(acetonitrile)dichloroplatinum and (2) rhodamine-123 of the formula:

2. The complex obtained by reacting potassium tetrachloroplatinate with rhodamine-123 of the formula:
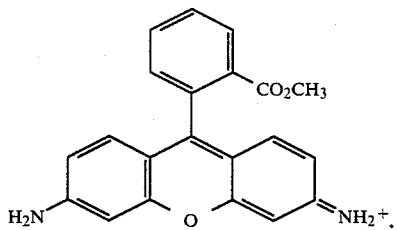
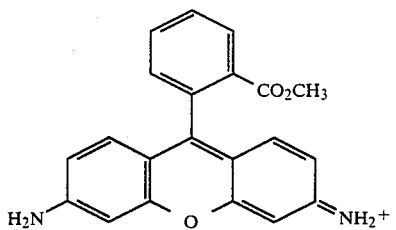
in a molar ratio of 1:1-2.
* * * * *